(12) United States Patent
Schultz et al.

(10) Patent No.: US 6,942,650 B1
(45) Date of Patent: Sep. 13, 2005

(54) EVACUATOR

(75) Inventors: Leonard S. Schultz, Bloomington, MN (US); Jeffrey K. Drogue, Minneapolis, MN (US); Kevin W. Gracie, Hopkins, MN (US)

(73) Assignee: Innovative Surgical Technologies, Inc., St. Louis Park, MN (US)

( * ) Notice: Subject to any disclaimer, the term of this patent is extended or adjusted under 35 U.S.C. 154(b) by 0 days.

(21) Appl. No.: 09/673,406

(22) PCT Filed: Apr. 15, 1999

(86) PCT No.: PCT/US99/08207

§ 371 (c)(1),
(2), (4) Date: Mar. 29, 2002

(87) PCT Pub. No.: WO99/53833

PCT Pub. Date: Oct. 28, 1999

Related U.S. Application Data (60) Provisional application No. 60/082,125, filed on Apr. 17, 1998.

(51) Int. Cl.[7] .................. A61M 1/00; B01D 46/00; F24C 15/20
(52) U.S. Cl. .................. 604/315; 604/313; 95/273; 454/66
(58) Field of Search ................ 604/313, 315, 604/35, 317; 95/273, 286; 606/115; 454/66; 126/299 F (56) References Cited

U.S. PATENT DOCUMENTS

| | | | |
|---|---|---|---|
| 3,604,421 A | * | 9/1971 | Pizzella ................ 604/335 |
| 4,111,753 A | * | 9/1978 | Folsom et al. ............ 435/3 |
| 4,921,492 A | | 5/1990 | Schultz et al. |
| 5,015,243 A | | 5/1991 | Schifano |
| 5,312,296 A | * | 5/1994 | Aalto et al. .............. 454/66 |
| 6,055,987 A | * | 5/2000 | Griesbach et al. ......... 128/849 |

OTHER PUBLICATIONS

Mangram AJ, Horan TC, Pearson ML, Silver LC, Jarvis WR. *Special Articles: Guidelines for Prevention of Surgical Site Infection, 1999*, AJIC Apr. 1999; 27(2):97-118, 100, 110-111, 118.

Enggaard TP, Moller-Larsen F. *Influence of local air suction on the density of air-borne bacteria during cementation of alloplasties*, Ugeskr Laeger Feb. 10, 1997; 159(7):952-5, National Library of Medicine www.ncbi.nlm.nih.gov.

Friberg B. *Ultraclean laminar airflow ORs*, AORN J Apr. 1998; 67(4):841-2, 845-51, National Library of Medicine www.ncbi.nlm.nih.gov.

Friberg BE, Friberg S, Burman LG. *Zoned vertical ultraclean operating room ventilation. A novel concept making long side walls unnecessary*, Acta Orthop Scand Dec. 1996; 67(6):578-82, National Library of Medicine www.ncbi.nlm.nih.gov.

(Continued)

*Primary Examiner*—Larry I. Schwartz
*Assistant Examiner*—Linh Truong
(74) *Attorney, Agent, or Firm*—Dorsey & Whitney LLP (57) ABSTRACT

An improved smoke evacuation system (10), a method for removing gaseous byproducts of surgical procedures, and noxious vapors from chemicals, is provided. The smoke, and vapor evacuation system includes a vacuum head (18) positioned at a surgical site or incorporated into a workstation. The vacuum head includes a plenum (28), a plenum support for preventing the plenum from collapsing when a vacuum or low pressure is established therein, and is adapted to facilitate the use of the system in a variety of surgical or commercial procedures at a variety of surgical sites or commercial workstations.

7 Claims, 10 Drawing Sheets

OTHER PUBLICATIONS

Cornet M, Levy V, Fleury L, Lortholary J, Barquins S. Coureul MH, Deliere E, Zittoun R, Brucker G, Bouvet A. *Efficacy of prevention by high-efficiency particulate air filtration or laminar airflow against Aspergillus airborne contamination durng hospital renovation, Infect Control Hosp Epidemiol* Jul. 1999; 20(7):508-13, National Library of Medicine www.ncbi.nlm.nih.gov.

* cited by examiner

EVACUATOR

The present application claims priority to a U.S. provisional patent application Ser. No. 60/082,125, filed Apr. 17, 1998.

BACKGROUND

This invention relates to equipment, systems and methods for the removal of gaseous and/or substantially gaseous material. Such material includes, but is not limited to aerosol byproducts of surgical procedures, including procedures involving cutting, heating or burning. More particularly, the present invention relates to an evacuator or vacuum head for an evacuation system that efficiently removes smoke, vapor, or plumes released by chemicals or produced by the use of lasers, sonic cutting and/or cautery at a surgical site.

Heating and/or burning of tissue during surgical procedures has become commonplace. An unwanted byproduct of such heating and/or burning, however, is the smoke generated thereby. Smoke plumes can obscure the surgeon's field of vision and the odor generated is unpleasant and distracting to the entire surgical team and to the patient, if awake. Moreover, the smoke plume may contain infectious agents that present a danger to persons in the operating room, and which can leave a lingering contamination within the operating area. Chemical vapor (e.g., such as that produced by the cleaning of computer parts) is, likewise, irritating to the respiratory tract of those who inhale it and may be carcinogenic.

Smoke evacuation and filtering systems have been developed to remove smoke plumes from surgical sites and chemical vapors from the work environment. Such systems typically include a hose connected to a vacuum source or generator and a suction wand connected to the hose. Various filtration systems have been used in conjunction with such vacuum generators to remove odor and infectious agents. Typically, the wand and hoses of known evacuation and filtration systems have required the constant attention or activity of an attendant to hold the wand or the nozzle of the hose close to the surgical site. Another problem is that the flow of air through the hose nozzle and the suction motor are sources of excessive and unwanted noise in the operating room or at the workstation.

More recently, at least in part to address the problems with wands, smoke evacuation systems may include an end effector that can be held in place at a surgical site without the constant attention of a nurse or other attendant. At least one such evacuation system and end effector is disclosed in U.S. Pat. No. 4,921,492 (Schultz et al.), the disclosure of which patent is incorporated herein by reference. Schultz et al. disclose an end effector for removing the gaseous byproducts of laser surgery from a surgical site. The end effector includes a flexible hose and a pliable vacuum head adhesively attachable in airtight relationship around a surgical site. The vacuum head includes a generally annular plenum for drawing plumes away from the surgical site from around a 360° arc. A porous plenum support prevents the flexible plenum from collapsing in the presence of a vacuum, and diffuses the vacuum around the entire periphery of the plenum.

U.S. Pat. No. 5,015,243 (Schifano) discloses another smoke evacuator including a flexible suction head for surrounding an operative site to draw smoke and air from around a perimeter of the site as smoke is produced. In one embodiment, the suction head is a doughnut shaped tubular member including a plurality of radial openings on an interior surface of the tubular member that faces the operative site. Schifano teaches that the tubular ring member may be circular or oval, and that it need not completely surround the operative site as long as air is drawn substantially in a surrounding fashion.

While smoke evacuation systems and end effectors of the Schultz et al. and Schifano type are well-suited for their intended purposes, there is room for improvement. For example, while the end effectors are pliable or flexible to conform to a surface to which they are attached, neither discloses a skeletal stiffening structure or frame for helping to maintain a conformed shape. Such a skeleton or frame would be valuable to adapt end effectors or vacuum heads for smoke evacuation for use on or near irregular physical features such as, for example, the ear, nose, mouth, or in the area of joints. It would also be advantageous if the generally central, site access opening of such end effectors could be varied in size to accommodate different sizes of incisions and different procedures, and if end effectors could be made available with the intake opening or openings in various locations, so that a particular end effector could be selected depending on the procedure to be performed. It would be advantageous if end effectors were available in a generally elongated, tubular shape bendable into a selected configuration by the user, and wherein the shaped or bent effectors would tend to remain in the selected configuration. It would also be advantageous if an end effector or vacuum head could be integrated with the widely used customary surgical drapes or drape material, or incorporated into part of a workstation that would contain noxious chemical fumes.

SUMMARY

The present invention provides an evacuator well-suited for removing or evacuating smoke, chemical vapors, aerosols, gaseous or generally gaseous material and fluids, including fluids with entrained particles or other material. It is well-suited for use in removing such substances from surgical sites, workstations and manufacturing assemblies or processing sites.

The needs outlined above are in large measure solved by a smoke evacuation system and method, including an evacuator, in accordance with the present invention. The embodiments described herein are designed to efficiently and quietly remove smoke or other aerosols, including smoke or bioaerosols generated during surgical procedures, and can be used at a surgical site without constant attention or manipulation by the surgeon or an attendant. They would also remove vapor from the work site.

An improved smoke evacuation system and method for removing gaseous byproducts of surgical or commercial procedures is provided by the present invention. The smoke evacuation system includes a vacuum head positionable at a surgical or other work site. The vacuum head includes a plenum, and a plenum support for preventing the plenum from collapsing when a vacuum or low pressure is established therein, and is adapted to facilitate the use of the system in a variety of surgical procedures at a variety of surgical sites.

In one embodiment, the present invention comprises a vacuum smoke evacuator head for coupling to a vacuum source for withdrawing generally gaseous byproducts, including smoke, fine particulate matter, air and the like, from a surgical or commercial site. The smoke evacuator head is substantially made of a generally pliable or flexible material and defines a plenum. A plenum support is carried within the plenum to provide support to the plenum and to prevent the plenum from collapsing when a vacuum or relatively low pressure area is established therein. The smoke evacuator head includes an open intake facing and/or intake openings, and may be positioned adjacent to or in a surgical site. An adhesive may be carried by the head for maintaining it in a selected position or location relative to the surgical site.

In one embodiment, the smoke evacuator head includes at least one access opening which may be selectively expanded in size. Typically, the access opening may be generally centrally located in the vacuum head, and has an initial peripheral edge which may be moved generally concentrically outwardly by selectively removing one or more removable, generally concentric peripheral portions extending substantially around the opening. Also typically, the opening, whether the initial size or one of the expanded sizes, may be covered or sealed before use by a removable film.

In another embodiment, the smoke evacuator vacuum head includes a skeletal stiffening member or positioning frame whereby the head may be configured and tends to remain in the selected configuration. The skeletal structure may comprise a single, flexible elongated member formed of a suitable material which may be bent or twisted, yet has sufficient rigidity to retain the selected bend or twist. The skeletal structure may be internal or external, and may comprise a single, elongated member, a single annular member, a plurality of axially aligned members, a number of parallel and/or branch members or a combination thereof. This embodiment may be well-suited for use in regions of the body having rather irregular surfaces such as joints, the ear, nose or mouth.

In another embodiment, the smoke evacuator may comprise a generally tubular body having two ends, one of which is adapted to be connected to another smoke evacuator vacuum head or to a coupling, such as a hose, for operably coupling the tubular body to a vacuum source. The other end may be free. The body may have one or more regions comprising openings or an open facing for admitting smoke and the like when a vacuum or low pressure is established in the body. In this embodiment, the body may have a stiffening element or a skeletal structure to allow the body to easily bend and remain in a particular shape for use in different situations. This embodiment of the vacuum head may be well-suited for use, as an adjunct or alone, in deep incisions or wounds during surgical procedures.

In yet another embodiment, the smoke evacuator vacuum head forms a plenum including a substantially open facing portion for being positioned generally adjacent to a smoke or aersol producing site. In one embodiment, wherein the plenum has a top, outwardly facing wall, is generally annular and includes a generally central access opening, the periphery of the opening being formed by an inner wall, the open facing may be formed in and/or adjacent to the inner wall comprising, for example, a bevel and/or a portion of the top wall. This embodiment is well-suited for use in surgical procedures during which a flap or ridge of skin or tissue may be formed, for example, around or as a result of the incision. Such procedures include plastic surgery procedures and mastectomies, for example, where the vacuum induced in the plenum may tend to pull skin flaps or tissue into it, particularly when the skin flap or tissue is held straight up.

In another embodiment, the evacuation system of the present invention comprises an evacuation hose for detachably connecting a vacuum generator or source and a vacuum head that generally surrounds a surgical site. The vacuum head is substantially made of a generally pliable or flexible material and defines a plenum having a generally central opening. A porous plenum supporting material is carried within the plenum to provide a degree of rigidity to the plenum and to prevent the plenum from collapsing when a vacuum or relatively low pressure area is established therein. The plenum includes an open facing region adjacent to the central opening. An adhesive may be carried by the skin contacting wall of the vacuum head for maintaining the vacuum head in place at a surgical site.

An embodiment and feature of the present invention is the concept of a foam supported channel of selectable cross-sectional area incorporated or integrated with a surgical drape, wherein the channel may be used to convey smoke and/or other aerosol debris away from a surgical site.

Any of the embodiments of the smoke evacuation system or vacuum head described herein may be provided in sterile form and in a color acceptable in an operating room environment.

In one embodiment, the smoke evacuation system of the present invention comprises a vacuum head end effector including generally contiguous, concentric areas or regions, which may be oval, formed or separated by generally concentric perforations whereby the areas may be selectively removed to correspond with required length of an incision or procedural area.

In one embodiment, the end effector in accordance with the present invention would have a pre-provided generally central and oval cutout of specific predetermined dimensions, the purpose of which would be to form a primary or initial work area, and to more easily allow the surgeon or attendant to remove surrounding peripheral oval sections to expand the original opening.

In one embodiment, each removable section of the vacuum head may be provided with a paper backed adhesive running on one surface of the sections. The paper backing would be removed once the size of the field or work area is determined, thereby allowing the remaining portion of the vacuum head and/or drape to affix to the patient's prepped skin or to the medical drape covering the intended site of the surgery.

In some embodiments, one or more manifold-like connection handles or tubes would extend from the foam filled channel or vacuum head to convey the smoke and vapor mixture from the operative site into a conduit and then to a collection, filtration and/or deodorization device wherein the mixture may be processed and the air may be returned to the room.

In some embodiments, the skin of the drape may cover the end effector, the manifold and the drape in continuity. In these and other embodiments, the manifold(s) may be provided to include either straight, i.e., parallel, and/or curved extension lips or walls that extend into or on either side of the plenum support that supports the outer walls of the plenum or evacuator vacuum head. The purpose of these lips or walls would be to prevent the possible kinking, narrowing or other form of occlusion by the covering skin of the drape at the plenum support/manifold interface or junction. This occlusion might be caused by the downward force placed on the manifold by the attached tubing that usually trails or falls to the floor of the operating room. In some instances, when suction or reduced pressure is applied without the lip extensions in place, the skin can invaginate and cover the entrance orifice of the manifold.

Another embodiment includes a chamber or gathering site for the evacuated smoke as it leaves the foam-filled channel or the plenum toward the exit site of the manifold or connection nozzle. The chamber is attached to the lip extensions or walls (described in the previous paragraph) at one end and forms or is attached to an exit port at the other end. The chamber and/or exit port may be adapted to increase flow velocities by including an area of decrease cross-sectional area. The exit port from which the smoke mixture leaves the smoke evacuator may be coupled to a typical conduit or hose.

Any of the embodiments disclosed herein may be formed by a wall or skin which may be made of the same as the material of a surgical drape. The skin typically would be fire retardant or resistant, and any of the embodiments may be preferably composed of bio-compatible material and be capable of disposition as such materials are typically disposed of.

It should be appreciated that features of any of the embodiments of the present invention may be selectively combined to adapt the smoke evacuator vacuum head for a variety of situations and surgical procedures.

Other features and advantages of the smoke evacuation device and method of the present invention will become more fully apparent and understood with reference to the following description and appended drawings and claims.

DETAILED DESCRIPTION

The accompanying Figures and this description depict and describe embodiments of the smoke evacuation system and method of the present invention, including the smoke evacuator vacuum head, and features and components thereof. As used herein, the terms "evacuator", "smoke evacuator", "end effector", "vacuum head" and like terms are intended to encompass a structure or structures into which gaseous or generally gaseous material, such as aerosols, smoke or vapor, is drawn when the structure is operably coupled to a source of low pressure or vacuum and placed generally adjacent to a site producing the gaseous or generally gaseous material. As used herein the term surgical field is intended to encompass places where an incision is to be made in the skin or where other surgical operations or procedures are to be performed. With regard to means for fastening, mounting, attaching or connecting the components of the present invention to form the device and system as a whole, unless specifically described otherwise, such means are intended to encompass conventional fasteners such as machine screws, nut and bolt connectors, machine threaded connectors, snap rings, hose clamps such as screw clamps and the like, rivets, nuts and bolts, toggles, pins and the like. Components may also be connected by adhesives, glues, welding, ultrasonic welding, and friction fitting or deformation, if appropriate. Unless specifically otherwise disclosed or taught, materials for making components of the present invention may be selected from appropriate materials such as metal, metallic alloys, natural and manmade fibers, vinyls, plastics and the like, and appropriate manufacturing or production methods including casting, extruding, molding and machining may be used.

Any references to front and back, right and left, top and bottom and upper and lower are intended for convenience of description, not to limit the present invention or its components to any one positional or spacial orientation.

Figure 1:
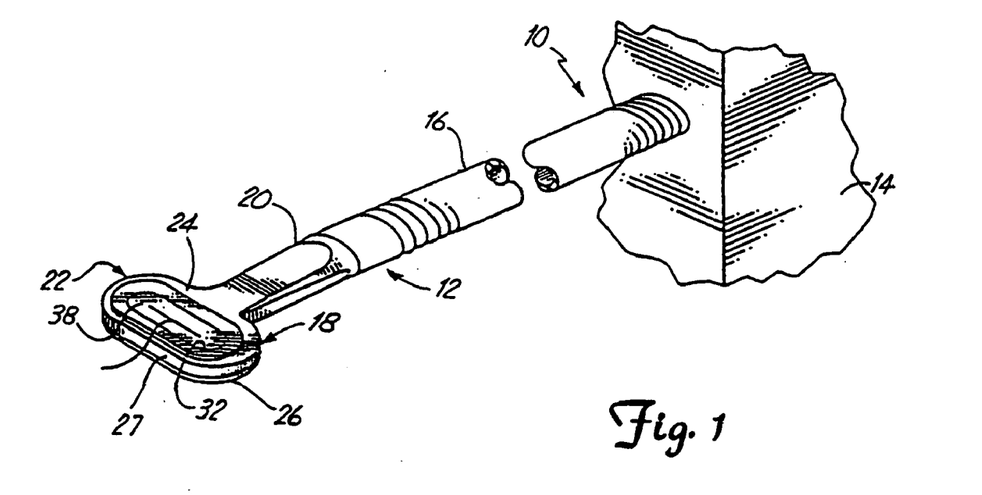
FIG. 1 is a fragmentary, perspective view of a smoke evacuation system including an vacuum head end effector.
Figure 2:
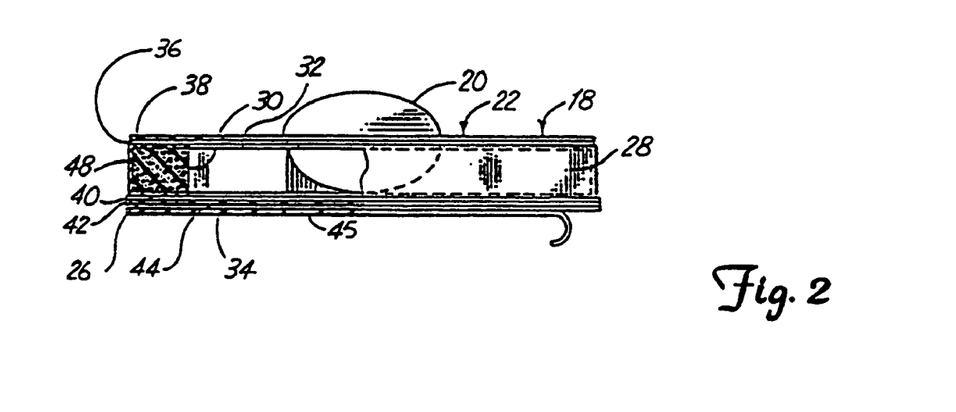
FIG. 2 is a front elevational view of the end effector shown in FIG. 1, with parts broken away for clarity.

Referring to FIGS. 1 and 2, a smoke evacuation system 10 in accordance with the above-noted Schultz et al. patent is depicted. The system includes an end effector 12 detachably connected to a suitable vacuum generator and filtration assembly 14. In one embodiment, the end effector 12 may include a flexible hose 16 coupled to a vacuum head 18 by a generally tubular manifold-like handle 20. In one embodiment, the vacuum head 18 includes a generally flat body 22 having a top wall 24, bottom wall 26 and outer sidewall 27 extending between the top wall 24 and bottom wall 26. The body 22 is preferably formed from a nonporous, pliable synthetic resin so that it will conform to the surface surrounding the surgical site. The top, bottom, and side walls 24, 26, 27 together substantially define a generally annular, internal plenum 28. The walls form an outer skin of the plenum 28 and may be composed of a medical grade, pliable, substantially non-porous material. The material of choice may be a synthetic, or it may be a natural material, such as fibrous material, e.g., cellulose or cotton fiber based material, such as presently used in surgical drapes and/or towels. The material of choice may be with or without flame-retardant characteristics. Preferred synthetic materials may be selected from open-celled foams, urethane film, spun lace polyester, nonwoven polyurethane tape and the like.

The top wall 24 includes an access aperture 32, and the bottom wall 26 includes access aperture 34, typically aligned and/or substantially congruent with the top wall access aperture 32. Preferably, a layer or adhesive 36 is carried by the top wall 24, and a clear film 38 is removably carried in place over the top access aperture 32 by the adhesive 36. Preferably, the bottom wall 26 includes a first adhesive layer 40 and a clear film 42 removably carried by the first adhesive layer 40. A second adhesive layer 44, which may have an antiseptic embedded therein, is carried by the bottom wall clear film 42. A sterile, peel-off shield 46 is removably carried by the antiseptic adhesive layer 44.

It will be appreciated that, upon application of a vacuum to the body 22, the top and bottom wall 24, 26 would be urged together, thereby reducing the volume of the plenum 28. Therefore, in the end effector 18 depicted in FIGS. 1 and 2, and in the embodiments of the invention described herein, an inner core plenum support 48 formed from a porous material such as foam urethane, or another appropriate reticulated, open-cell foam material, a supporting matrix, or the like, is carried within plenum 28, to provide the body 22 with some rigidity without substantially detracting from the flexibility of the vacuum head 18. The inner core 48 comprises an inner plenum supporting structure 48 that permits the flow of air and smoke into the plenum 28 while blocking the ingress of larger materials such as tissue or surgical materials. Preferably, the inner core support 48 should be made of a synthetic or natural material that is hydrophobic so that it will resist absorption of fluids often present in the operative field. A reticulated open cell foam of a size between 5 and 25 pores per inch (ppi) is well-suited for the inner core. In another embodiment, the plenum support core 48 may be molded and/or may be formed contiguously with the outer skin, and may be provided with a plurality or matrix of airflow shafts or channels.

Whether the shape of vacuum head 18 is generally circular, generally oval or a different shape, it will be noted that the plenum 28 provides for evacuation of generally gaseous material substantially around a complete 360° arc.

Figure 3:
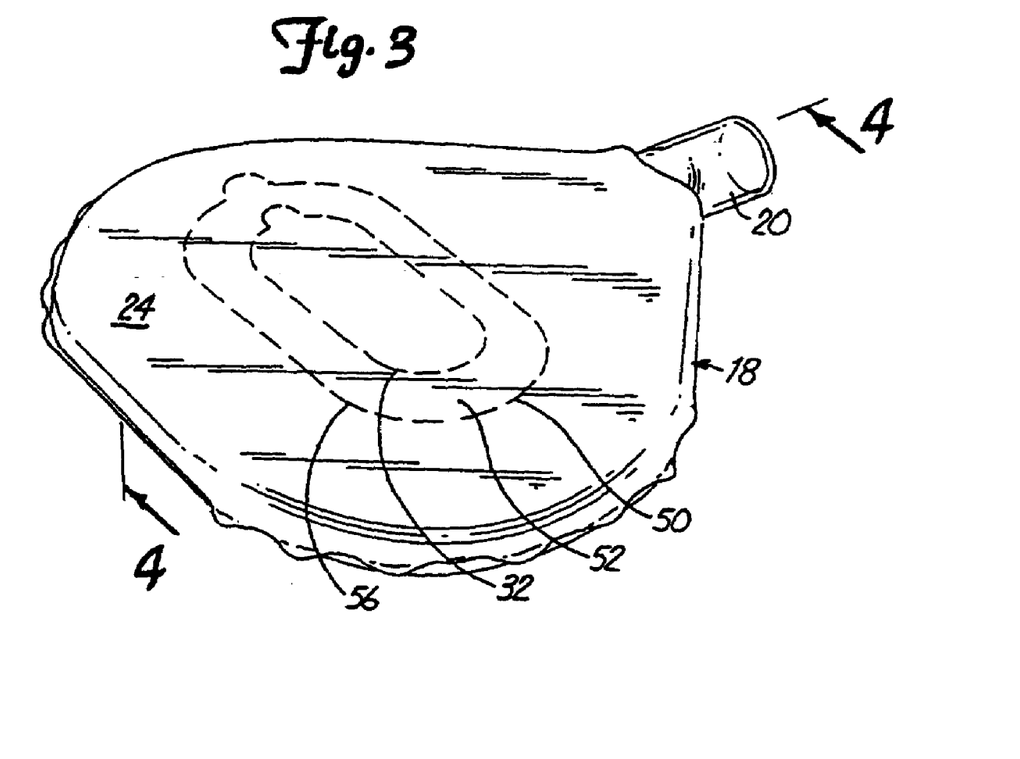
FIG. 3 is a top perspective view of an embodiment of the end effector vacuum head in accordance with the present invention.
Figure 4:
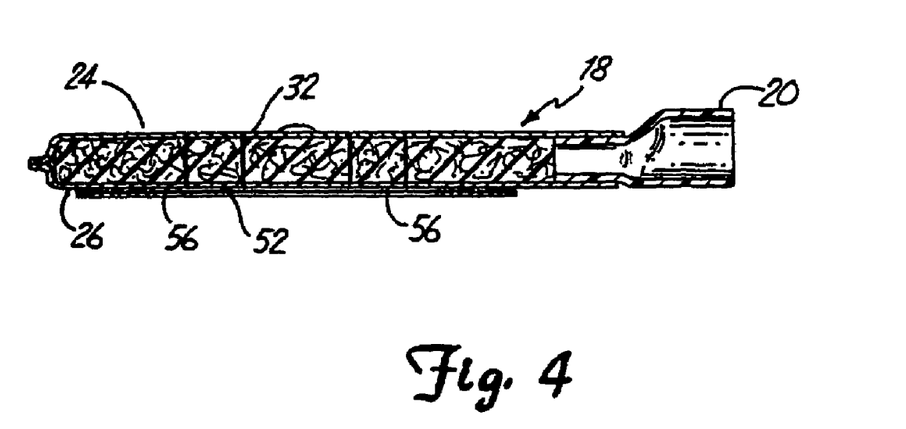
FIG. 4 is a side elevational view of the end effector vacuum head depicted in FIG. 3.

FIGS. 3 and 4 depict an embodiment of the smoke evacuator 18 of the present invention, wherein the central access aperture 32 is expandable to form a larger size aperture or opening 50 by removing a peripheral portion 52 of the evacuator vacuum head 18 from around the originally provided access aperture 32. The top and bottom walls 24, 26 and the plenum support material 48 may include a line of weakness 56, be scored, cut or partially cut to define the removable portion 52 and to facilitate its removal. A selected number of generally concentric removable portions may be provided. The line of weakness, scoring, cut or perforations 56 may be substantially concentric and congruent with respect to the initial access aperture 32, or they may be adapted to expand the initial access aperture in a selected direction or into a selected shape, e.g., they may comprise one or more arcs of weakness beginning and ending at the peripheral edge of the access opening (see, for example, lines of weakness a and b shown in FIG. 6). (In describing this and other embodiments, features in common with the end effector depicted in FIGS. 1 and 2, and with other embodiments of the invention, are and will be commonly referenced.)

Figure 5:
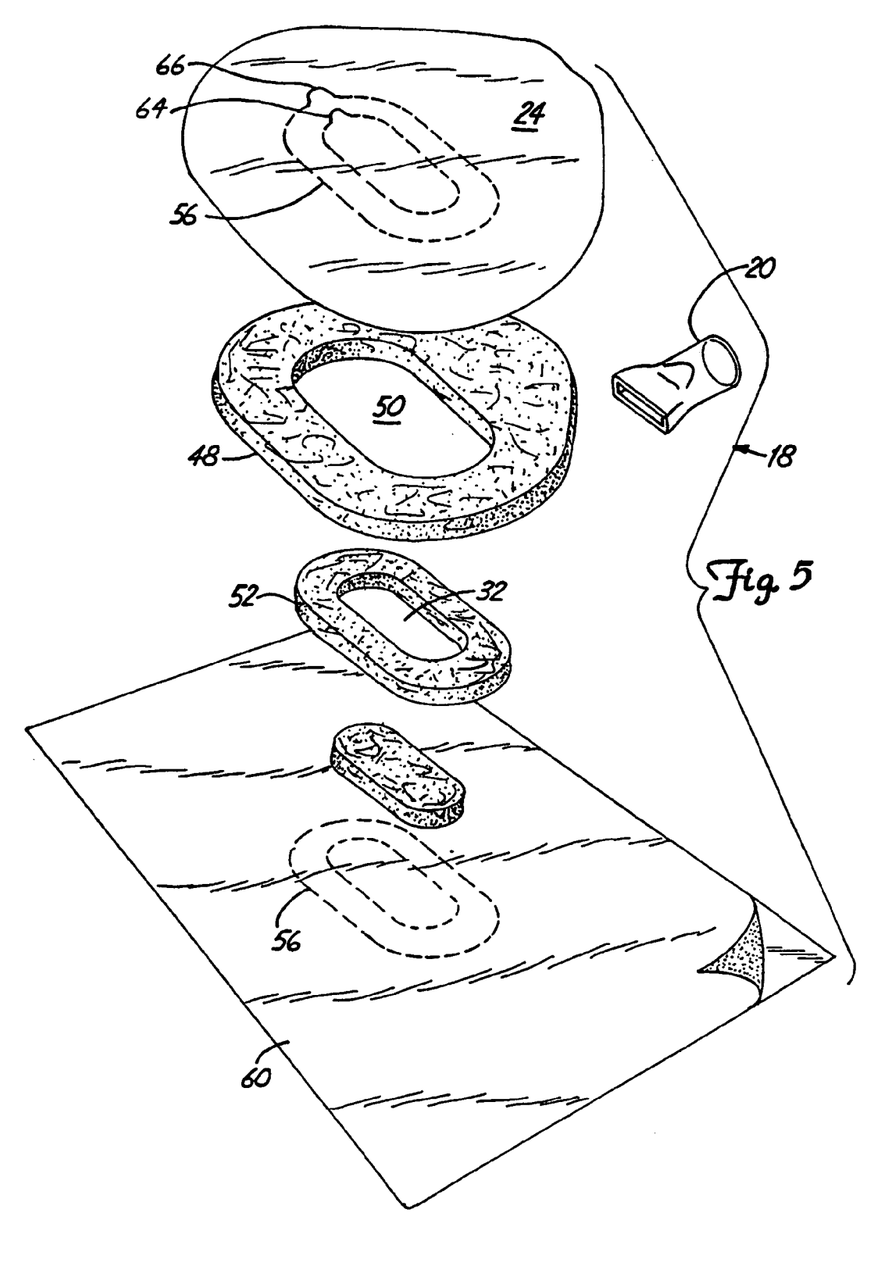
FIG. 5 is an exploded perspective view of another embodiment of the present invention.
Figure 6:
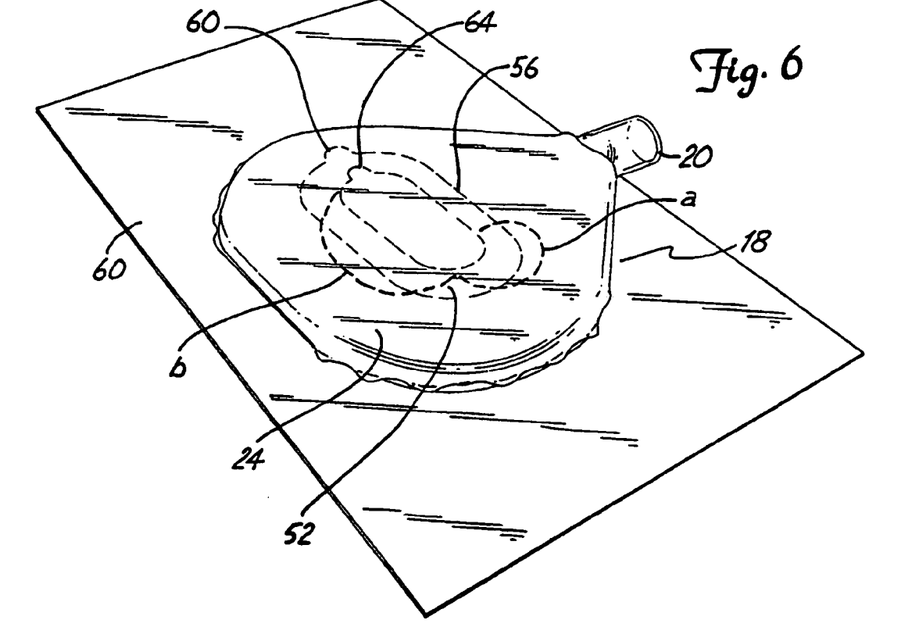
FIG. 6 is a perspective view of the embodiment depicted in FIG. 5.
Figure 12:
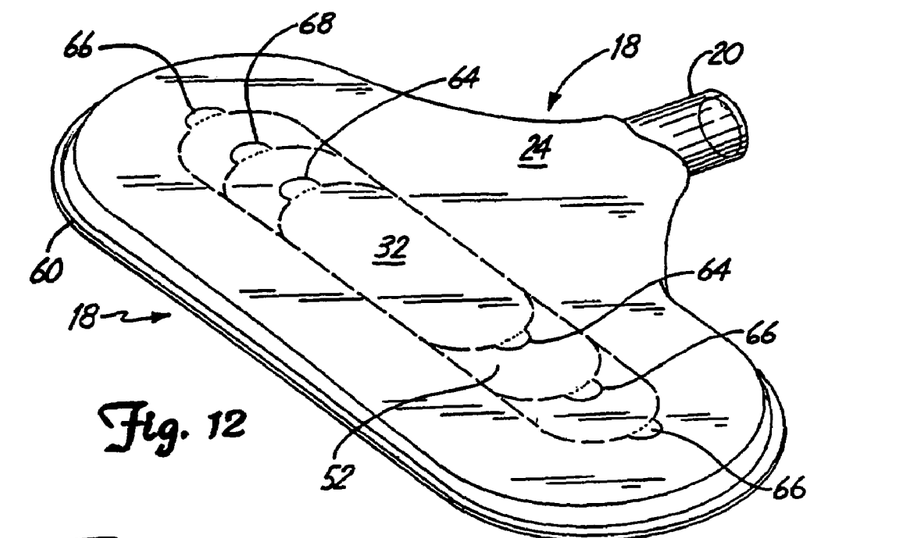
FIG. 12 is a perspective view of another embodiment of the present invention.

FIGS. 5, 6 and 12 depict another embodiment of the smoke evacuator vacuum head 18 of the present invention, wherein the vacuum head 18 is provided with a variable size access aperture, and is integrated with a surgical drape 60 comprising a relatively large, flexible, generally cloth-like sheet material. Such a drape or drapes are widely used to establish or set off a surgical field, may be generally transparent, and may be formed by a PVC material or the like. They may carry an adhesive on one surface for connection to the skin of a patient, typically, four strips of adhesive to define a periphery. One surface of the drape may have an adhesive thereon for attachment to the vacuum head end effector 18. Integration of the vacuum head end effector 18 of the present invention may be accomplished by providing a drape or piece of drape material with an opening, placing the end effector 18 over the opening, and attaching or sealing the edges of the end effector 18 to the drape (see FIG. 6). The bottom wall of the end effector 18 may be omitted, in which case the top or outside side wall 24 may be joined to the drape, whereby the drape forms the bottom wall, completing the plenum 28 and encompassing the open-cell, reticulated foam forming the plenum support 48. In use, the integrated drape and end effector 18 may be placed over an intended incision site with the access opening aligned with the site. A tab 64 may be grasped and pulled to permit access to the site. If a larger incision site opening is required initially, or if the incision site needs to be expanded or extended, another tab 66 may be grasped and pulled to remove a peripheral portion 52, thereby enlarging, specifically lengthening, the opening. As depicted in FIG. 12, the pre-cut access opening covering is provided with as many tabs as convenient to facilitate grasping and pulling the covering away from the end effector 18. Pulling one of the tabs releases the pre-perforated covering skin and allows the pre-cut foam 48 to be removed.

Figure 7:
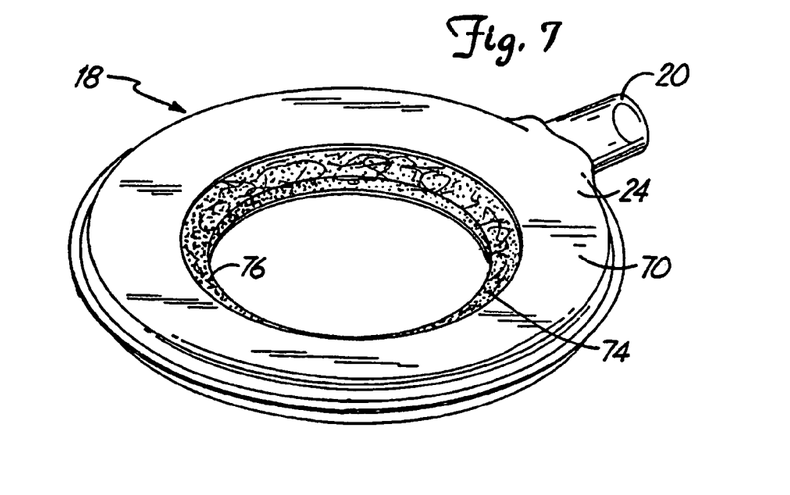
FIG. 7 is a perspective view of another embodiment of the present invention.

FIG. 7 (and others, including FIGS. 15 and 16) depict another embodiment of the present invention wherein a wire-like skeletal member 70 is provided. The skeletal member 70 is flexible and bendable to the degree that it may be manipulated, bent or twisted into a desired shape, yet it is inflexible or rigid enough to retain its bent or twisted shape. It may be located in the plenum 28 as shown, or it could be appropriately secured to the exterior of the end effector 18.

Figure 8:
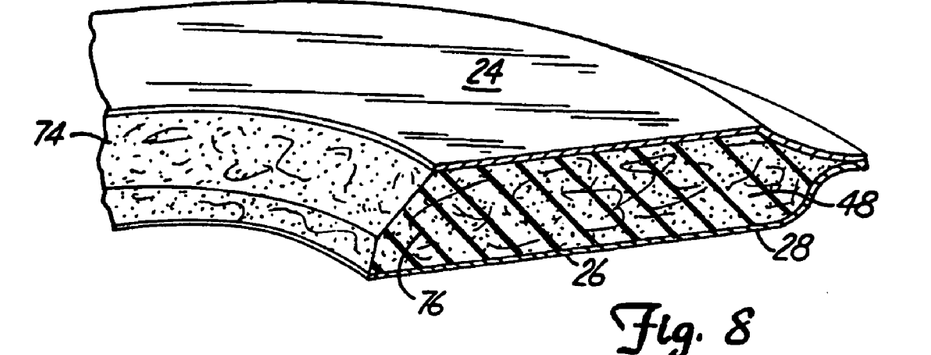
FIG. 8 is a fragmentary perspective view of another embodiment of the present invention.
Figure 9A:
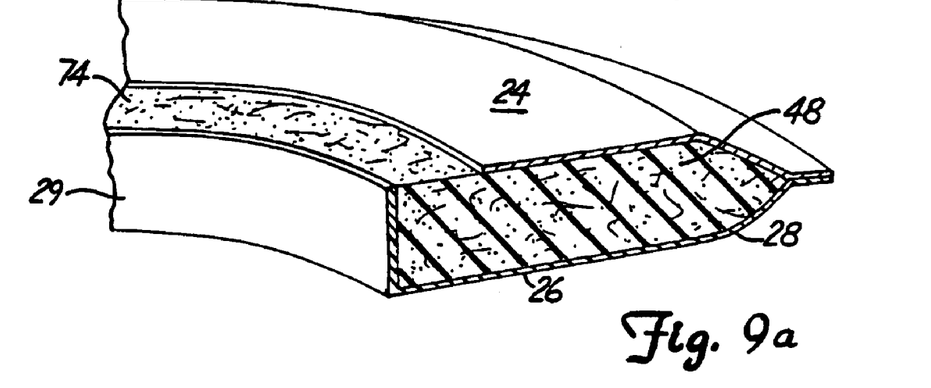
FIG. 9a is a fragmentary perspective view of another embodiment of the present invention.
Figure 9B:
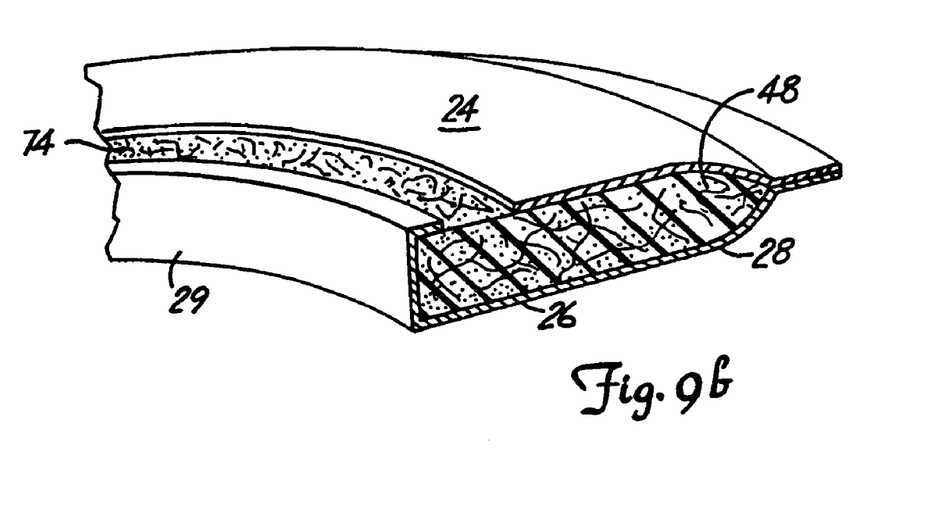
FIG. 9b is a fragmentary perspective view of another embodiment of the present invention.
Figure 10:
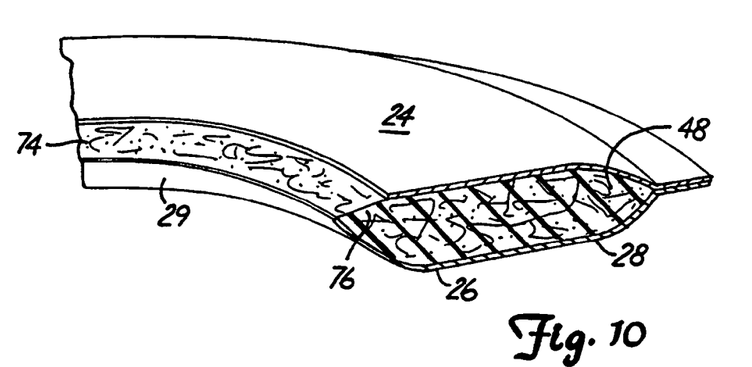
FIG. 10 is a fragmentary perspective view of another embodiment of the present invention.

FIG. 7, and FIGS. 8–10, depict embodiments of the present invention wherein the walls of the plenum 28 defining the access opening or aperture is an open facing 74, and wherein the open facing 74 extends into the top wall 24 of the plenum 28. As shown in FIGS. 7 and 8, the access opening wall is substantially completely an open facing 74 which extends upwardly at an angle or bevel 76 into the top wall. The bias or angle into the top wall may be from 10 to 60 degrees, with 45 degrees well-suited for many procedures. FIGS. 9a and 9b depict two unbeveled embodiments, and FIG. 10 depicts an embodiment wherein the inside wall of the plenum 28 is substantially continuous, only the bevel 76 comprising the open facing portion of the plenum 28. These embodiments generally are well-suited for use in surgical procedures involving a flap or ridge of tissue which, if the top wall or a portion thereof was not adapted to provide an intake for gaseous material, might occlude the open facing, blocking or at least interfering with the flow of the gaseous material into the plenum 28. The embodiment depicted in FIG. 10 may be further adapted for particular surgical procedures, such as procedures involving the breast, by providing a sealing means, such as an adhesive, on the inside rim or wall 29 of the plenum 28 so it can be adhered or sealed in place to the breast with a portion of the breast extending through the access opening.

Figure 11:
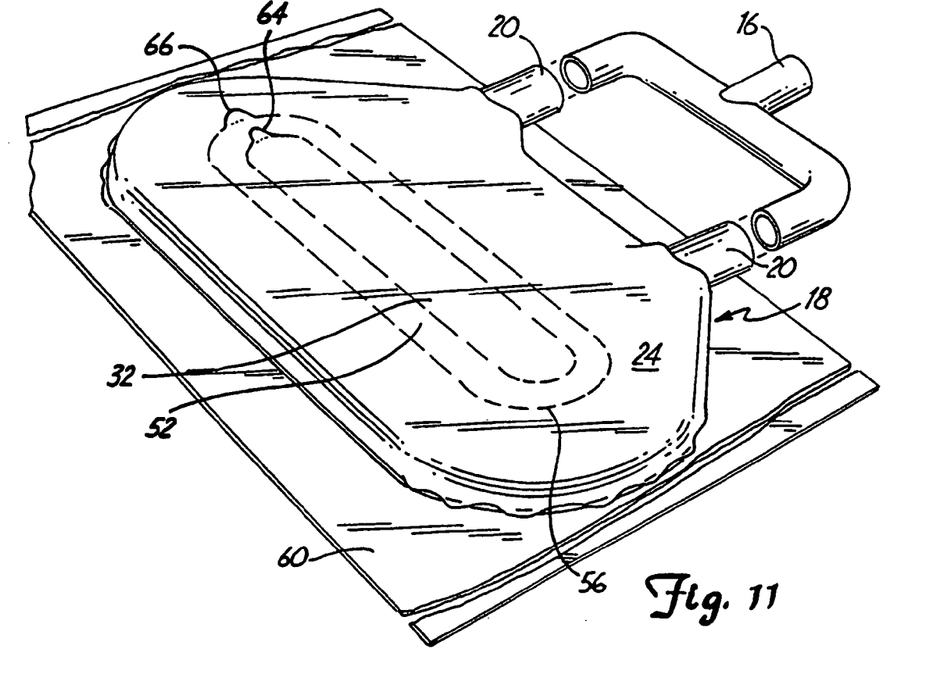
FIG. 11 is a perspective view of another embodiment of the present invention.

FIG. 11 depicts a drape/smoke evacuator embodiment of the present invention wherein dual vacuum coupling attachment handles are provided. Such an embodiment may be well-suited for procedures requiring large incisions, such as spinal procedures, thoracotomy, large abdominal incisions and the like. In one embodiment, the evacuator embodiment of FIG. 11 may be used as a stand alone device without a drape as depicted in FIG. 11.

Figures 13, 14:
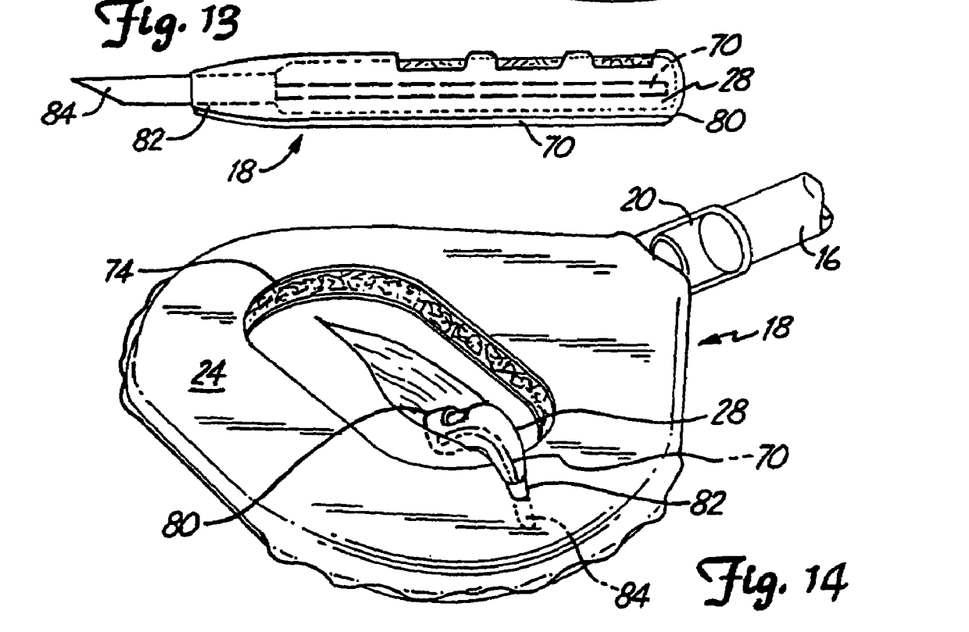
FIG. 13 is a perspective view of another embodiment of the present invention.
FIG. 14 is a perspective view of another embodiment of the present invention.

FIGS. 13 and 14 depict another embodiment of the smoke evacuator of the present invention wherein the plenum 28 is formed by a substantially continuous wall, which may be a single piece of extruded material or which may be formed from joined top, bottom and side walls. In this embodiment, the vacuum head 18 and the plenum 28 have a generally tubular, straight, elongated shape with two free ends, one end 80 of which may be closed and the other end 82 which may be adapted to be coupled to another embodiment of the end effector 18 of the invention, as shown in FIG. 14. The end 82 adapted to be coupled is provided with a sharpened, cannula-like member 84 for penetrating the wall of the plenum 28 as shown in FIG. 14. The end 82 may be flattened or otherwise adapted to be similarly attached to suction tubing or to the above described channel. In one embodiment (not shown), the cannula-like member 84 is not sharpened as depicted in FIG. 13. In other embodiments (not shown), this embodiment of the invention may be adapted for direct coupling to a hose or other fitting, or may include or be attached to a manifold or handle 20 generally similar to that shown in FIG. 1, for coupling to a hose or other fitting. Note that FIG. 14 also depicts that the stiffening skeletal member 70, shown in two of its possible locations, may be used to configure and position the generally tubular smoke evacuator 18 embodiment, or a portion thereof, in a relatively deep incision or wound.

Figure 15:
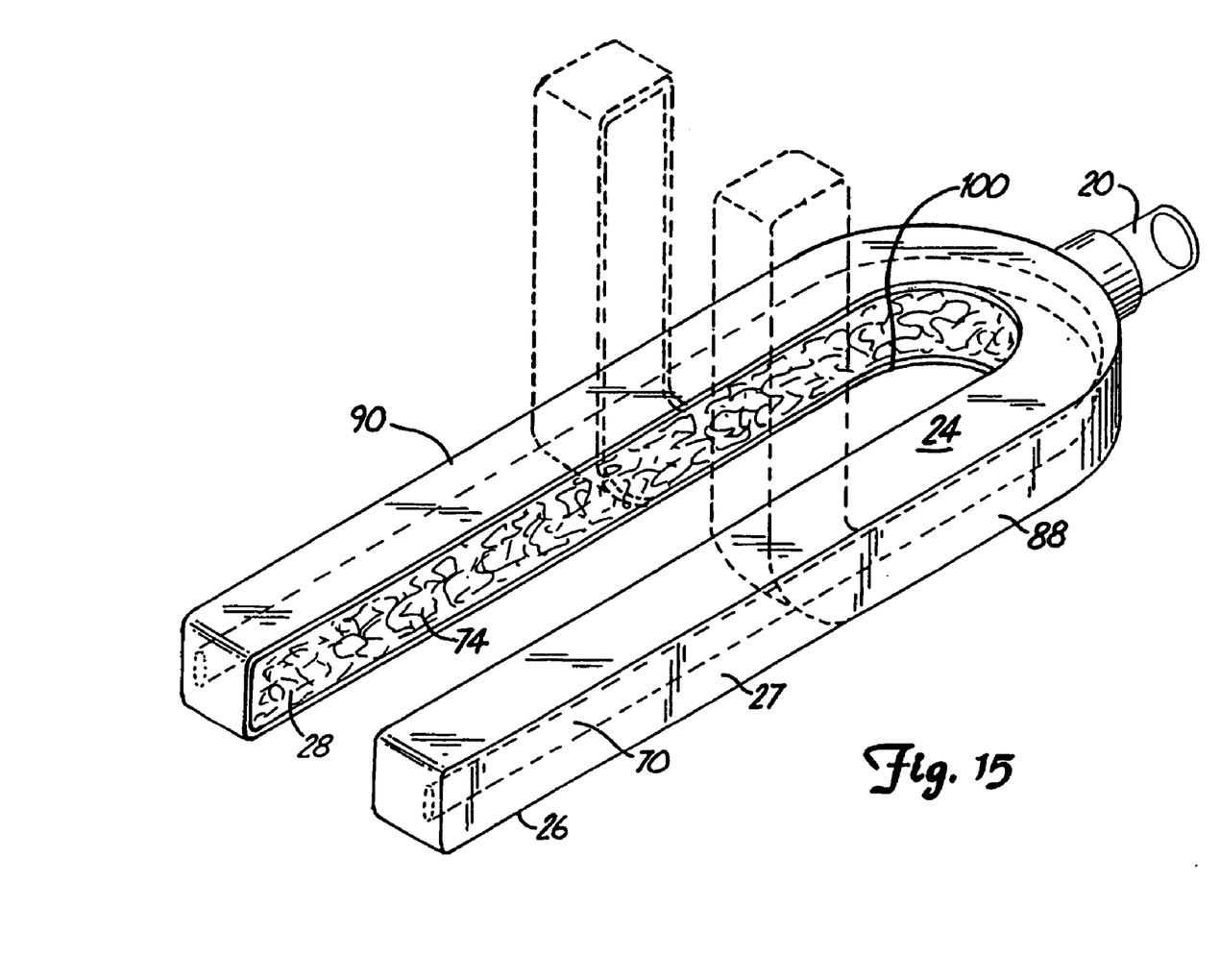
FIG. 15 is a perspective view of two embodiments of the present invention as they might be used in conjunction.

FIG. 15 depicts an embodiment of the smoke evacuator of the present invention adapted for spinal operations or other procedures wherein a relatively long incision may be used. The plenum 28 is formed in the shape of two generally parallel tubular members 88, 90, each having substantially continuous top, bottom, outside and end walls, and an inside wall comprising an open facing 74. Each embodiment of the invention may include a generally enlarged internal plenum space adjacent to the manifold port or handle 20. In the evacuator of FIG. 15, for example, the top wall 24 and bottom wall 26 are extended to form an enlarged plenum space 100 adjacent the manifold port or handle 20, such that the suction force generated at the manifold or handle 20 is more evenly dispersed, including throughout the plenum and along the open facing 74. Such a feature may be included in any of the embodiments of the invention described herein. Note that, as in all the embodiments described herein, the malleable, skeletal stiffening member 70, which might be formed of nitinol or similar "memory" material, may be incorporated to facilitate re configuring this embodiment to, for example, the configuration shown in phantom. This embodiment of the vacuum head 18 may have a single connection manifold or nozzle 20 as shown, or it may be adapted to have two manifolds with a circuit adapter to permit them both flow into a single ⅞" vacuum hose (see, for example, FIG. 11). Such circuit adapters are readily available as standard catalog items for respiratory therapy and anaesthesia.

Figure 16:
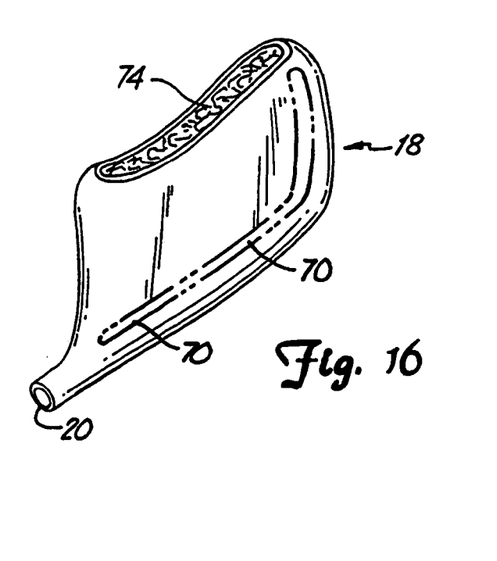
FIG. 16 is a perspective view of another embodiment of the present invention.

FIG. 16 depicts an embodiment of the smoke evacuator 18 well-suited for use in dental surgery, e.g., a "bite-block" embodiment. It should be appreciated that the smoke evacuator 18 maybe provided in any configuration suitable for use in or around the mouth, and that substantially the entire skin or walls forming this embodiment would preferably be non-absorbent.

Figure 17:
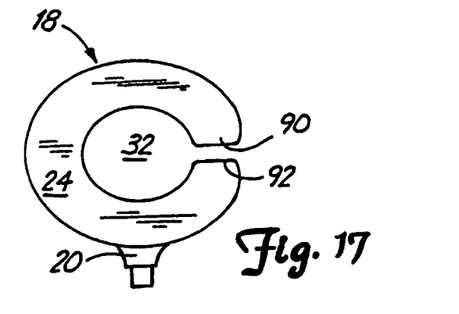
FIG. 17 is a perspective view of another embodiment of the present invention.
Figure 18:
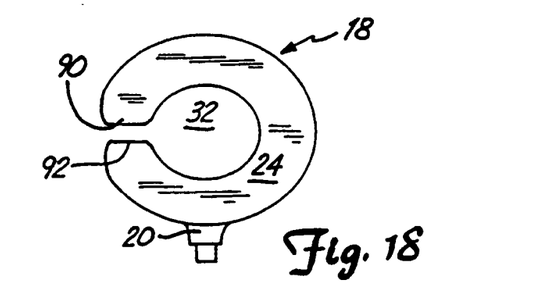
FIG. 18 is a perspective view of another embodiment of the present invention.

FIGS. 17 and 18 depict an embodiment wherein a generally tubular vacuum head 18 comprises an internal plenum region adjacent to the manifold port or handle 20 and two plenum arms 90, 92. The two plenum arms 90, 92, which, as in FIGS. 17 and 18, may be two free arms, may be curled or curved to substantially surround a surgical site. An advantage of this embodiment is that the plenum arms 90, 92 with their free end are flexible, whereby the head 18 is made more flexible so it may more easily assume and conform to the shape of the underlying tissue. The arms 90, 92, and thus the head 18, may move in various directions according to the layout of adjacent tissues. Because, in one embodiment, one surface of the vacuum head 18 of FIGS. 17 and 18 may have an adhesive attached thereto for attachment to a drape, it may be desirable to have one embodiment wherein the ends 90, 92 face one direction when viewed from the top and another embodiment wherein the ends 90, 92 face the other direction. These embodiments may provide for the flexibility needed for various surgical procedures, including procedures on bilateral, mirror image structures or tissues.

In use, it should be understood that operation of all the embodiments disclosed herein may be generally similar. The vacuum head 18, or the drape 60 with the vacuum head 18 integrated, is detachably affixed to the skin surrounding a surgical site by peeling off the sterile peel-off shield 46 and pressing the adhesive layer 44 carried by the bottom wall 26 of the body 22 against the skin. It will be appreciated that the flexible vacuum head 18 permits a complete, airtight seal of the bottom wall 26 against the skin or any skin covering (such as a clear drape). The films 28, 42 carried by the top and bottom walls 24, 26, respectively, can be entirely removed. Upon actuation of the vacuum source 14, air is drawn into the plenum 28, and is transported through the flexible hose 16 and into the filter (not shown) in the vacuum source 14. The porous plenum support 48 carried within plenum 28 prevents plenum 28 from collapsing under the influence of the vacuum. The plenum support 48 also may be adapted to enhance the effect of diffusing the vacuum around or through the plenum 28, thereby enhancing the drawing air into the plenum 28 around its entire periphery or open facing, rather than solely in the vicinity of handle 20. Moreover, drawing air through the larger opening presented by the plenum 28 reduces the noise created by the flow of air into hose 16. Gaseous or aerosol material produced at the surgical site is thereby drawn into the plenum 28 and evacuated through flexible hose 16. The plenum support 48, due to its porous nature, also may act as a filter as the smoke is drawn through it.

Referring back to FIG. 1, surgical instruments can be manipulated through the tear line T in clear film 38 and/or through the access opening 32. Alternatively, the clear film 38 can be completely removed. It will be appreciated that the vacuum, and drawing effect, presented by the plenum 28 to the surgical site may be increased by leaving the clear film 38 in place.

The end effector(s) 18 of the present invention may be extruded from a single piece of material, e.g., the body 22, tubular handle 20, flexible hose 16, and in some embodiments, a filter and connector, may be formed from a unitary piece of synthetic resin or similar extrudable material. The end effector(s) 18 of the present invention may be advantageously and hygienically disposed of after a single use, without the necessity of handling contaminated material.

Figure 19:
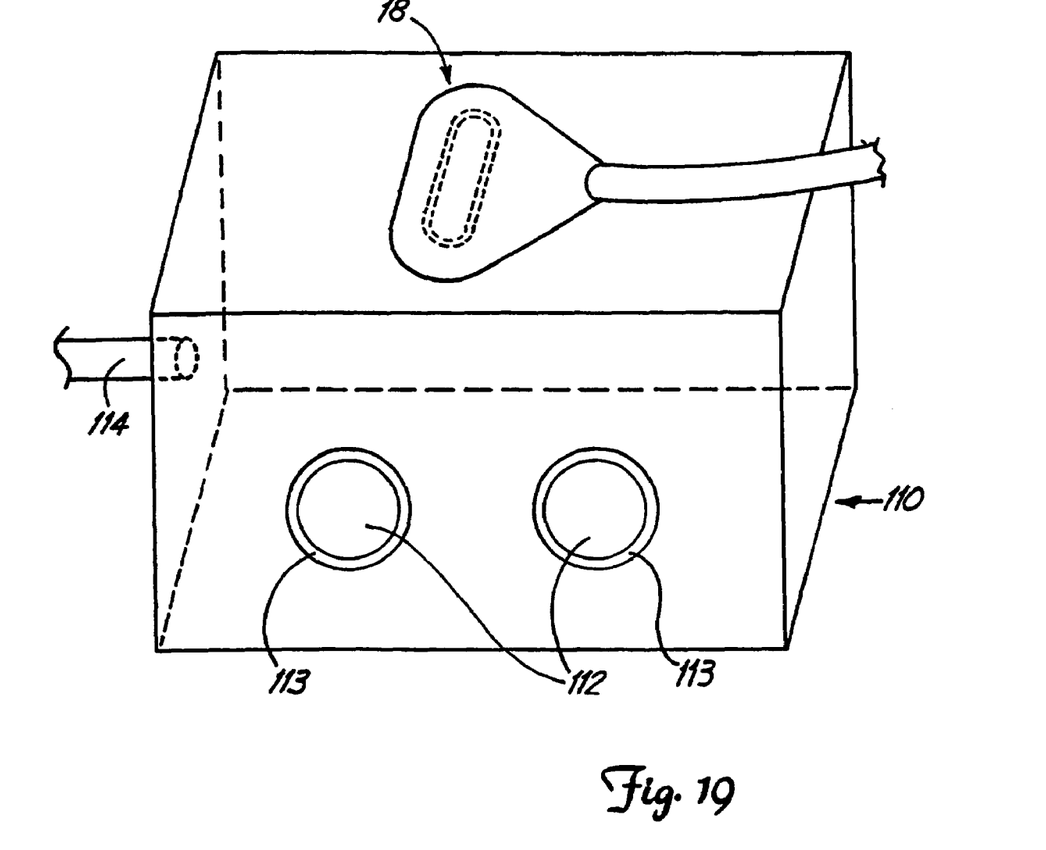
FIG. 19 is a perspective view of an embodiment of the invention in use in a workstation.

In another use of the invention, the embodiments of the vacuum head 18 may be used at a workstation or the like, or on or in a containment vessel or the like, in order to remove fumes or smoke. Such workstations and vessels may be used, for example, for cleaning components in the computer industry or for performing experiments or tasks in which noxious fumes are emitted. FIG. 19 shows such a use. The workstation 110 may have hand holes 112, with or without suitable sealing collars 113 or attached gloves (not shown), through which a technician or user may put their gloved or ungloved hands. The vacuum head 18 may be positioned in, adjacent to or on the workstation 110, for example, as depicted, it may be coupled to an exterior surface of the workstation enclosure adjacent to an opening in the wall defining the workstation. It may also be coupled to an interior surface. When a suction force is applied to the vacuum head 18, the vacuum head 18 receives smoke or fumes from the inside of the workstation. In one embodiment, an air supply may be pumped into the workstation 110 through a hose 114 to help urge the vapors, aerosols or gaseous material toward the vacuum head 18. Such an air supply may provide air at any given rate; one such rate for a typical-sized work station may be 30 cubic feet per minute.

The present invention may be embodied in other specific forms without departing from the essential spirit or attributes thereof. The described embodiments should be considered in all respects as illustrative, not restrictive.

What is claimed is:

1. An apparatus for removing smoke, airborne particulates, gases or like by-products of operating or commercial procedures producing such by-products, comprising:
    a plenum having a top wall, a bottom wall spaced apart from said top wall, a first side wall extending between said top and bottom walls and presenting an outer periphery of said plenum, and a second side wall extending between said top and bottom walls and presenting an inner periphery of said plenum, a structure defining a generally open facing adjacent to the inner periphery of said plenum, said walls defining an internal plenum chamber in fluid communication with said open facing;
    vacuum means operably coupled to said plenum for creating a reduced pressure within said plenum chamber, thereby drawing said by-products through said open facing;
    a support carried within said plenum chamber for maintaining said top and bottom walls in spaced apart relationship and distributing said reduced pressure along the open facing of said plenum whereby said by-products are drawn through said open facing from about said site; and
    a piece of fabric-like sheet material, said apparatus operably coupled to said piece of material.

2. An apparatus for removing smoke, airborne particulates, gases or like by-products of operating or commercial procedures producing such by-products, comprising:
    a plenum having a top wall, a bottom wall spaced apart from said top wall, a first side wall extending between said top and bottom walls and presenting an outer periphery of said plenum, and a second side wall extending between said top and bottom walls and presenting an inner periphery of said plenum, a structure defining a generally open facing adjacent to the inner periphery of said plenum, said walls defining an internal plenum chamber in fluid communication with said open facing;
    vacuum means operably coupled to said plenum for creating a reduced pressure within said plenum chamber, thereby drawing said by-products through said open facing;
    a support carried within said plenum chamber for maintaining said top and bottom walls in spaced apart relationship and distributing said reduced pressure along the open facing of said plenum whereby said by-products are drawn through said open facing from about said site; and
    a piece of malleable material operably coupled to the plenum.

3. An apparatus for removing smoke, airborne particulates, gases or like by-products of operating or commercial procedures producing such by-products, comprising:
    a plenum having a top wall, a bottom wall spaced apart from said top wall, a first side wall extending between said top and bottom walls and presenting an outer periphery of said plenum, and a second side wall extending between said top and bottom walls and presenting an inner periphery of said plenum, a structure defining a generally open facing adjacent to the inner periphery of said plenum, said walls defining an internal plenum chamber in fluid communication with said open facing said bottom wall including an adhesive layer for adhesive attachment of said apparatus around a surgical site;
    vacuum means operably coupled to said plenum for creating a reduced pressure within said plenum chamber, thereby drawing said by-products through said open facing; and
    a support carried within said plenum chamber for maintaining said top and bottom walls in spaced apart relationship and distributing said reduced pressure along the open facing of said plenum whereby said by-products are drawn through said open facing from about said site.

4. An apparatus for removing smoke, airborne particulates, gases or like by-products of operating or commercial procedures producing such by-products, comprising:
    a plenum having a top wall, a bottom wall spaced apart from said top wall, a first side wall extending between said top and bottom walls and presenting an outer periphery of said plenum, and a second side wall extending between said top and bottom walls and presenting an inner periphery of said plenum, a structure defining a generally open facing adjacent to the inner periphery of said plenum, said walls defining an internal plenum chamber in fluid communication with said open facing, said plenum being generally annular, said inner periphery defining an access aperture for providing access to the plenum generally inside said inner periphery;
    vacuum means operably coupled to said plenum for creating a reduced pressure within said plenum chamber, thereby drawing said by-products through said open facing; and
    a support carried within said plenum chamber for maintaining said top and bottom walls in spaced apart relationship and distributing said reduced pressure along the open facing of said plenum whereby said by-products are drawn through said open facing from about said site.

5. The invention according to claim 4, including a generally transparent film removably carried by said top wall across said access aperture.

6. The invention according to claim 5, said plenum further comprising a removable portion adjacent to the access aperture whereby the access aperture may be expanded.

7. An apparatus for removing smoke, airborne particulates, gases or like by-products of operating or commercial procedures producing such by-products, comprising:
    a plenum having a top wall, a bottom wall spaced apart from said top wall, a first side wall extending between said top and bottom walls and presenting an outer periphery of said plenum, and a second side wall extending between said top and bottom walls and presenting an inner periphery of said plenum, a structure defining a generally open facing adjacent to the inner periphery of said plenum, said walls defining an internal plenum chamber in fluid communication with said open facing, wherein said plenum contains free ends to provide for flexibility of use of the apparatus;

vacuum means operably coupled to said plenum for creating a reduced pressure within said plenum chamber, thereby drawing said by-products through said open facing; and a support carried within said plenum chamber for maintaining said top and bottom walls in spaced apart relationship and distributing said reduced pressure along the open facing of said plenum whereby said by-products are drawn through said open facing from about said site.

* * * * *